(12) United States Patent
Lou et al.

(10) Patent No.: US 9,271,943 B2
(45) Date of Patent: Mar. 1, 2016

(54) ARSENIC COMPOUND SOLUTION AND ALBUMIN NANOPARTICLE AND LYOPHILIZED PREPARATION ENTRAPPING ARSENIC COMPOUND PREPARED USING SAME

(75) Inventors: Lanhua Lou, Zhejiang (CN); Yongsheng Fan, Zhejiang (CN); Chengping Wen, Zhejiang (CN)

(73) Assignee: ZHEJIANG CHINESE MEDICAL UNIVERSITY, Zhejiang (CN)

( * ) Notice: Subject to any disclaimer, the term of this patent is extended or adjusted under 35 U.S.C. 154(b) by 0 days.

(21) Appl. No.: 14/129,250

(22) PCT Filed: Jan. 5, 2012

(86) PCT No.: PCT/CN2012/070047
§ 371 (c)(1),
(2), (4) Date: Dec. 24, 2013

(87) PCT Pub. No.: WO2013/082875
PCT Pub. Date: Jun. 13, 2013

(65) Prior Publication Data
US 2014/0370119 A1    Dec. 18, 2014

(30) Foreign Application Priority Data
Dec. 7, 2011    (CN) .......................... 2011 1 0403008

(51) Int. Cl.
| | |
|---|---|
| *A61K 33/36* | (2006.01) |
| *A61K 31/285* | (2006.01) |
| *A61K 9/51* | (2006.01) |
| *A61K 9/19* | (2006.01) |
| *A61K 38/38* | (2006.01) |

(52) U.S. Cl.
CPC ................. *A61K 9/5169* (2013.01); *A61K 9/19* (2013.01); *A61K 9/5192* (2013.01); *A61K 33/36* (2013.01); *A61K 38/38* (2013.01)

(58) Field of Classification Search
None
See application file for complete search history.

(56) References Cited

U.S. PATENT DOCUMENTS

| | | | |
|---|---|---|---|
| 3,981,782 A * | 9/1976 | Bradford et al. ............... 205/266 |
| 2004/0126434 A1* | 7/2004 | Kumana ................. A61K 33/36 |
| | | | 424/623 |

FOREIGN PATENT DOCUMENTS

| | | |
|---|---|---|
| CN | 1370540 A | 9/2002 |
| CN | 1698650 A | 11/2005 |
| CN | 1723029 A | 1/2006 |
| WO | WO 2004/032822 A2 | 4/2004 |

OTHER PUBLICATIONS

Fan, Jibo, "Study of the Preparation of $As_2O_3$ Albumin Nanospheres and the Effect of the EJ Cells," *The Master's Thesis of Guangxi Medical University*, May 1, 2010, p. 1-71, Abstract p. 4-6.

Yang, Zhiwen et al., "A Study on the Preparation and Antitumor Efficacy of Human Serum Albumin (has) Nanoparticles Containing Arsenous Oxide Bearing Monoclonal Antibody," *Chinese Archives of Traditional Chinese Medicine*, Aug. 2007, vol. 25, No. 8, p. 1633-1635, Abstract.

\* cited by examiner

*Primary Examiner* — Jeffrey T Palenik
(74) *Attorney, Agent, or Firm* — Saliwanchik, Lloyd & Eisenschenk

(57) ABSTRACT

An arsenic compound solution, and an albumin nanoparticle and a lyophilized preparation prepared using same and entrapping an arsenic compound. The arsenic compound solution is prepared using the following method: adding $As_2O_3$ powder in sterile deionized water to obtain a suspension, 6 to 25 mg of $As_2O_3$ powder being added in every mL of sterile deionized water; dripping an NaOH solution to the obtained suspension until the powder is fully dissolved and adjusting the pH of the solution to 7.5 to 9, and making the concentration of the obtained arsenic compound solution be 5 to 20 mg/mL in terms of the added $As_2O_3$. The albumin nanoparticle is prepared by mixing an albumin solution and the arsenic solution and the arsenic solution with the mass ratio of the added $As_2O_3$ in arsenic compound solution to the albumin ranging from 1:5 to 1:20 and using a method of solvent removing and physical curing.

3 Claims, 6 Drawing Sheets

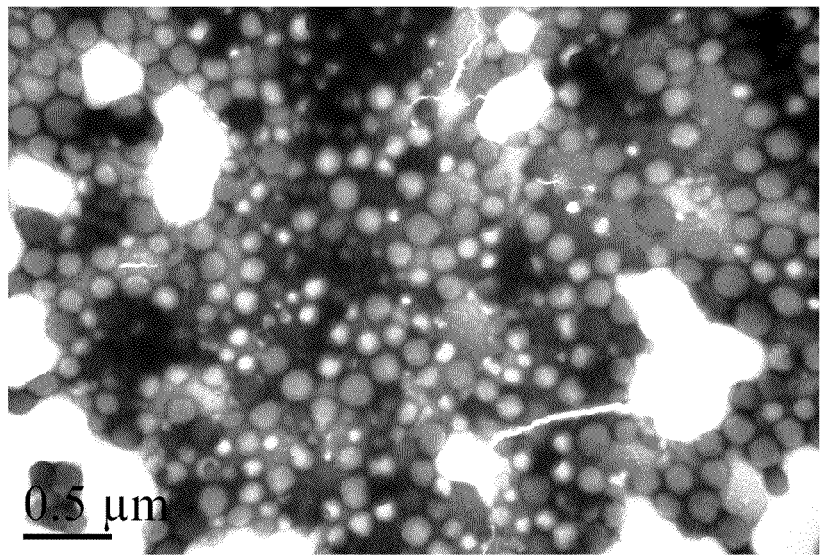
Figure 1
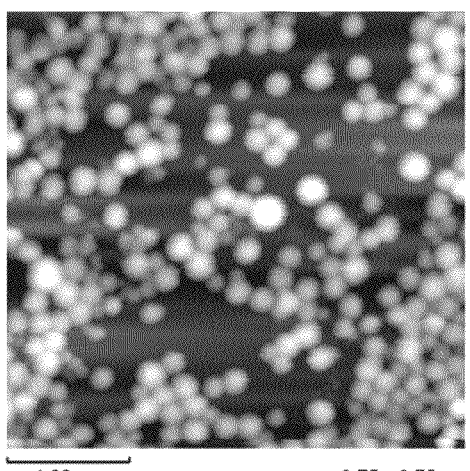
Figure 2A1
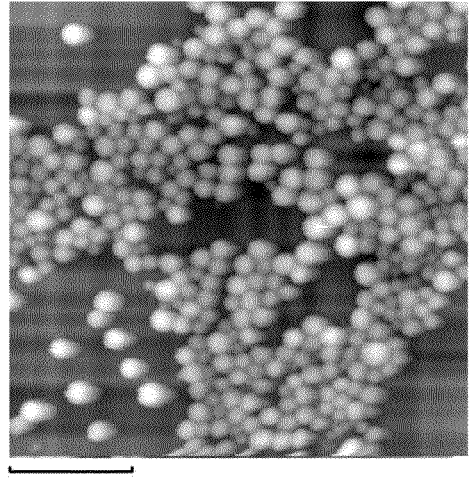
Figure 2A2
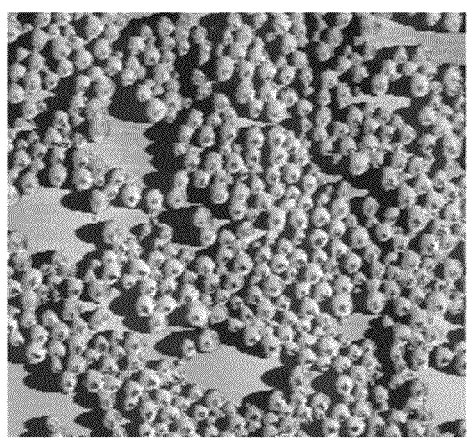
Figure 2A3
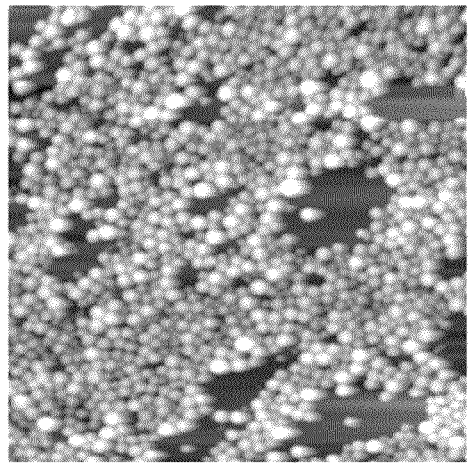
Figure 3

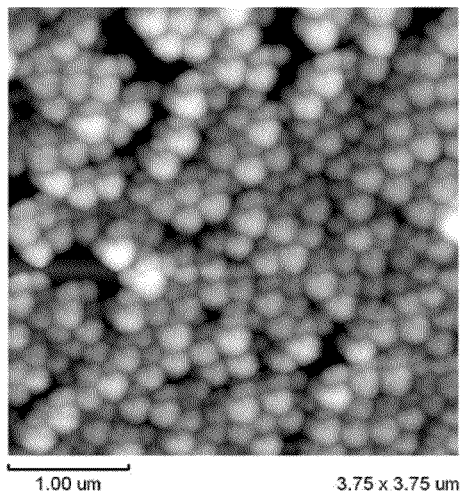
Figure 4A1
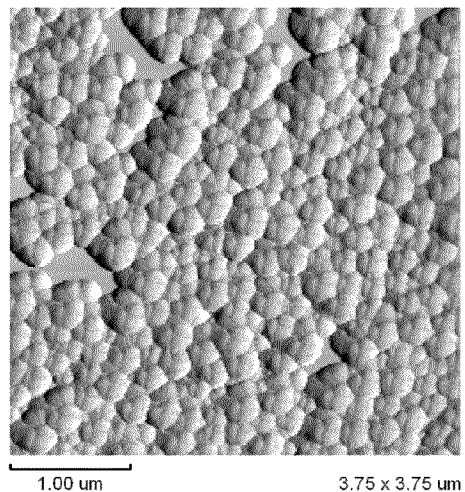
Figure 4A2
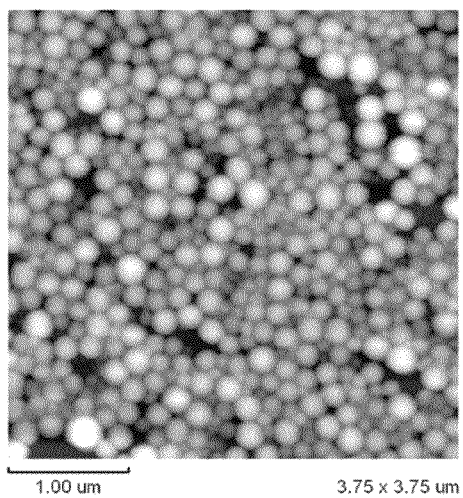
Figure 4A3
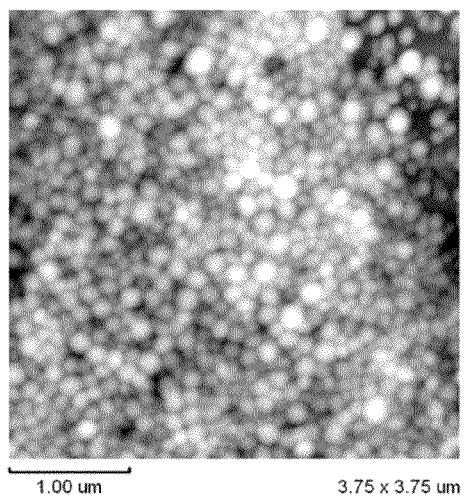
Figure 5A
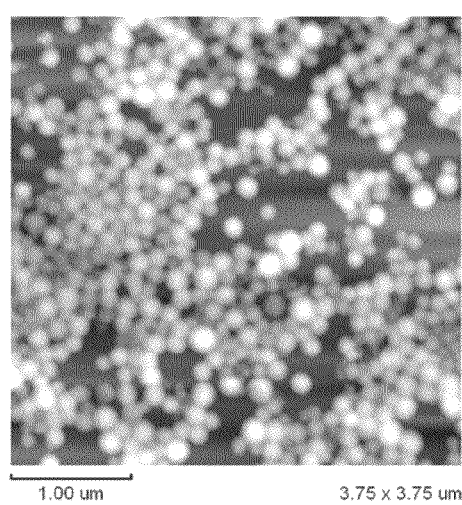
Figure 5B

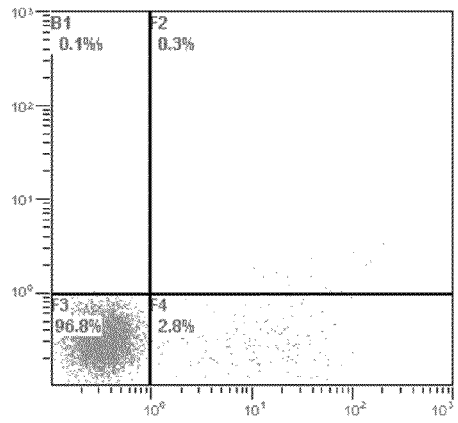
Figure 10A
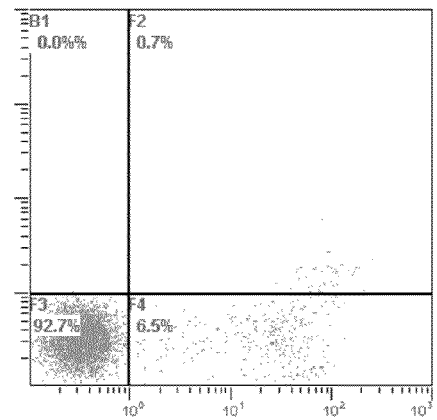
Figure 10B1
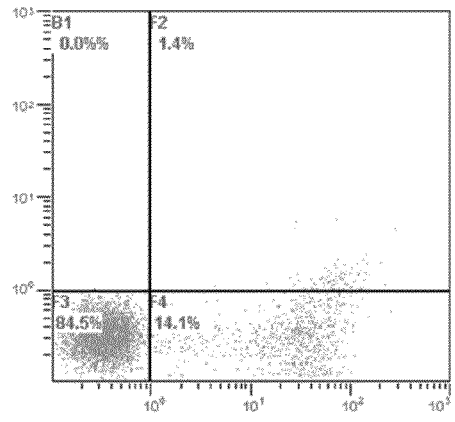
Figure 10B2
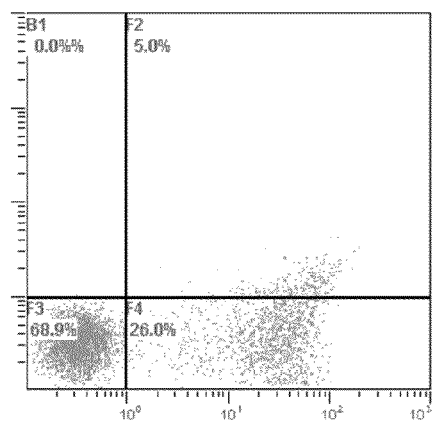
Figure 10B3
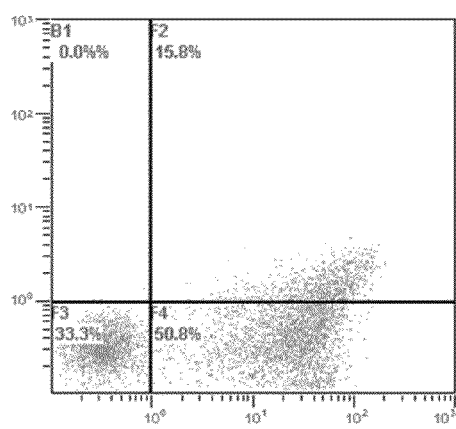
Figure 10B4
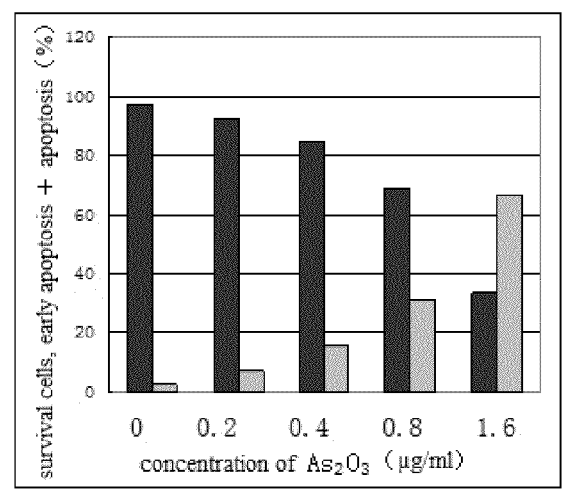
Figure 11

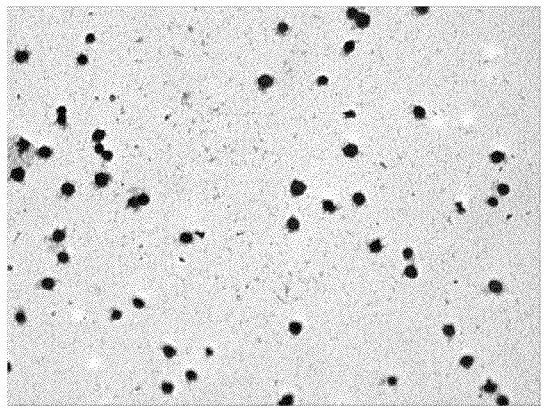 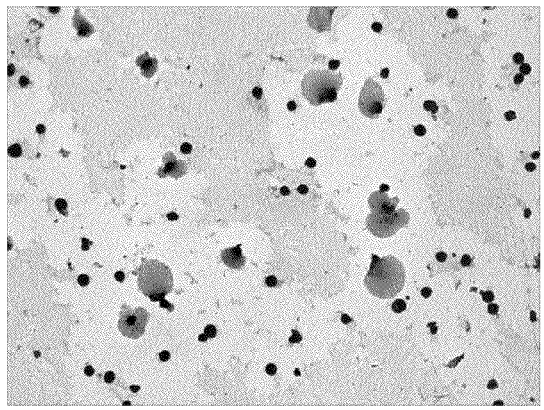
Figure 12A             Figure 12B
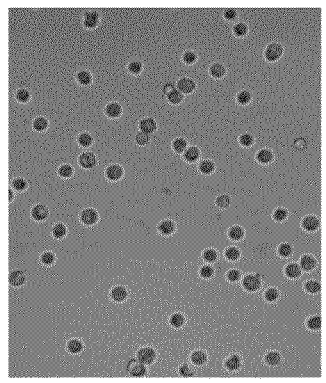 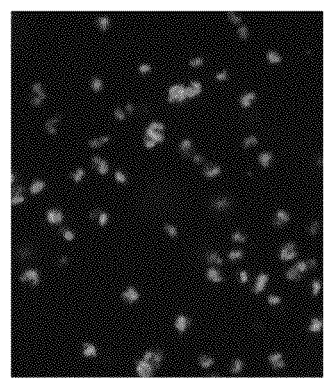 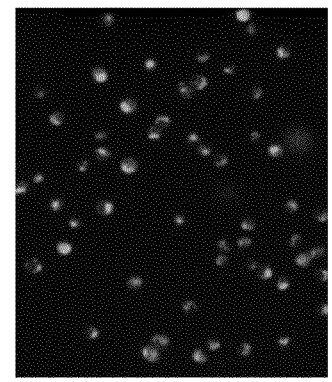
Figure 13A             Figure 13B             Figure 13C
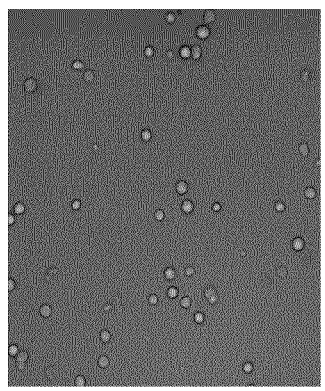 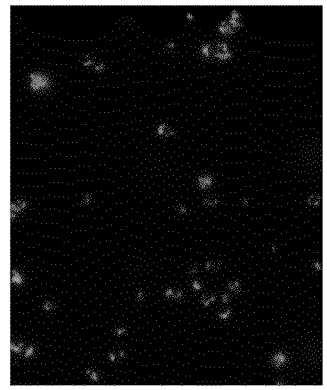 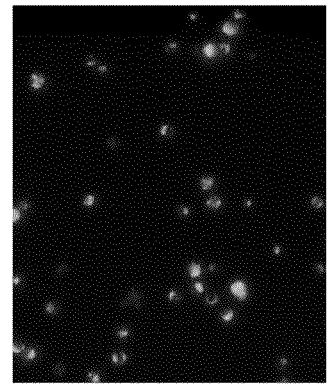
Figure 14A             Figure 14B             Figure 14C

ARSENIC COMPOUND SOLUTION AND ALBUMIN NANOPARTICLE AND LYOPHILIZED PREPARATION ENTRAPPING ARSENIC COMPOUND PREPARED USING SAME

CROSS REFERENCE TO A RELATED APPLICATION

This application is a National Stage Application of International Application Number PCT/CN2012/070047, filed Jan. 5, 2012; which claims priority to Chinese Application No. CN 201110403008.9, filed Dec. 7, 2011; which are incorporated herein by reference in their entirety.

FIELD OF THE INVENTION

The invention relates to an aqueous solution of arsenic compound, arsenic compound-loaded albumin nanoparticles and a freeze-dried preparation of arsenic compound-loaded albumin nanoparticles prepared with the arsenic compound solution.

BACKGROUND INFORMATION

Systemic lupus erythematosus (SLE) is an autoimmune disease that can affect systems and organs throughout the body. The pathogenesis is unknown, but in the numerous cases, it is considered to be an autoimmune rheumatic disease activated by polyclonal B cell in vivo and autoantibodies against autoantigens. Western medicine treatment of SLE currently mainly involves glucocorticoids and cytotoxic drugs or immunosuppressive agents; Even though these methods can prolong a patient's survival, long-term usage or high-dosages of such hormones can cause gastrointestinal bleeding, osteoporosis, infections and other complications, which cause many complications for the treatment. Therefore, it is urgent to study an effective and reliable, minimal side-effect and economical drug treatment, to meet the different needs of patients.

$As_2O_3$, commonly called arsenic trioxide, is highly toxic, but is a compound with a wide range of functions. It has a long medical history in China, and has been used for the treatment of psoriasis, syphilis, rheumatism, and certain maladies. As a traditional Chinese medicine, arsenic was first an invention and contribution of great significance in the field of drug development and treatment of leukemia, and was universally acknowledged. In recent years, because $As_2O_3$ plays a significant role in acute promyelocytic leukemia treatment, many scholars have conducted in-depth studies on the drug which has demonstrated that $As_2O_3$ can treat a broad range of tumors. Not only does it have excellent inhibitory effect on leukemia cells, but it also is effective against many solid tumors, including lung cancer, pancreatic cancer, esophageal cancer, ovarian cancer, stomach cancer, colon cancer and so on.

Many scholars in China and abroad have intensely studied the structure of arsenic through the scope of modern medicine. Studies have shown that arsenic, in a trivalent state, works in vivo. Trivalent arsenic is a complexing agent of thiol (—SH), and can inhibit metabolic?? activity (of what) after interaction with thiol in the interior of enzyme molecule, which induces apoptosis through a number of pathways, demonstrating that $As_2O_3$ is very effective against tumors. Wei Yaming etc. (Northwest Military Medical Journal, 2002, 23 (5): 324-326.) reported dual effects of As2O3 on apoptosis and differentiation of leukemia cells. $As_2O_3$ is found that lower concentration of $As_2O_3$ has no effect on expression of differentiation antigen of NB4 and HL-60 cell lines, and only high concentration of $As_2O_3$ treated for more than 72 h could play effects of both apoptosis and differentiation. Meanwhile, mechanism of action of $As_2O_3$ on cytokines and immuno-modulatory has also caused extensive concerns, some studies: Zhu Xiaochun, etc. (Chinese Journal of Internal Medicine, 2001, 40 (11): (764-765); (Chinese Journal of Rheumatology, 2002, 6 (5):343-346) postulated that $As_2O_3$ could control or reduce autoimmune responses by inducing apoptosis of autoreactive lymphocytes and play an important role in inhibiting the pathogenesis of SLE.

However, there are still many problems in the traditional clinical application of $As_2O_3$, such as high toxicity, and low bioavailability, etc. At present, the clinically used preparation is through an arsenious acid injection made from $As_2O_3$. After intravenous administration, as elevated arsenic concentrates in plasma and rapidly diffuses into the surrounding tissue, side effects including but not limited to: gastrointestinal symptoms, peripheral neuritis, dry skin, pigmentation, even renal damage or ascites can occur in the patient. Since safe dose of $As_2O_3$ systemic administration is very limited and the difference between a safe dose and a toxic dose is infinitesimally small, which limits its application as a chemotherapeutic agent.

Therefore, when seeing the clinical value of $As_2O_3$ medicine, if we can improve the traditional preparation process, and adopt modern technology to prepare new $As_2O_3$ nanoparticles, thereby increasing the bioavailability, reducing drug dosage and toxicity, and improving efficacy, it will have important clinical significance.

The existing preparing process of nanoparticles preparation containing $As_2O_3$:

1. Zhou Jie et al (Chinese Journal of New Drugs 2005 14 (1) 54) disclosed a process for preparing arsenic trioxide-albumin microspheres through a method of emulsion-glutaraldehyde solidification; this method not only uses a large amount of organic solvent and oil, but also requires more chemical crosslinking agents-glutaraldehyde, the residual of which will bring some potential safety hazard to the application of preparations. 2. Chenhua Jiang (Second Military Medical University 2007.28 (6) 644) disclosed a process for preparing arsenic trioxide albumin microspheres by an emulsification-heat solidification method; 3. Yang Zhiwen, etc. (Traditional Chinese Medicine 2007 25 (8) 115) disclosed a process for preparing arsenic trioxide albumin microspheres by a emulsification-heat-stabilization method, which requires castor oil, cottonseed oil, and large amounts of organic solvent for removing the oily residue. The latter two methods, either an emulsion-glutaraldehyde solidification method or an emulsification—heat-stabilization method, have complicated technical processes and are unsuitable techniques for mass-production.

In the initial research phase of preparing arsenic compound-loaded nano-particles it was found, through many trials, that the particle size of nanoparticles prepared by a emulsion-heat-solidification method using castor oil could vary greatly, with a complicated technical process; and then it is switched to a desolvation-glutaraldehde chemical solidification method, but due to a large specific surface area of nano-particles, the nanoparticles having not been solidified easily merge into big grains large clumps during stirring, which increases the likelihood of cross-linking between nanoparticles. The prepared particle will be too large, have a relatively short release time, contain residual glutaraldehyde chemical reagents, and require complicated technical processes, making it unviable for industrial production.

In summation, the prior art has complicated technical processes; hidden danger from residual toxic reagent glutaraldehyde; and a short release time, poor stability, poor storage stability, etc. There is an urgent need to develop a new process for preparing $As_2O_3$ loaded nanoparticles preparation.

SUMMERY OF THE INVENTION

The first objective of this invention is to provide an aqueous solution of arsenic compound, which has well-defined structure and good drug effects.

To solve the above technical problems, the technical scheme adopted in this application is as follows:

An arsenic compound solution is prepared according to the following method: adding $As_2O_3$ powder in sterile deionized water to obtain a suspension, in which 6 to 25 mg of $As_2O_3$ powder are added in every mL of sterile deionized water; dripping an NaOH solution to the obtained suspension until the powder is fully dissolved and adjusting the pH of the solution to 7.5 to 9, and making the concentration of the obtained arsenic compound solution be 5 to 20 mg/mL in terms of the added $As_2O_3$.

The $As_2O_3$ powder used in this invention is of purity ranging from 95% to 99.9%.

In the present invention, $As_2O_3$ is dissolved in a sodium hydroxide solution, and the concentration and volume of the sodium hydroxide solution are controlled to adjust the pH value of the resulting arsenic compound solution, as opposed to using hydrochloric acid to adjust the pH value of the arsenic compound solution expressed in the conventional method. It is recommended to dissolve $As_2O_3$ in a 1 mol/L to 6 mol/L (preferably 1 mol/L to 2 mol/L) sodium hydroxide solution, after $As_2O_3$ has completely dissolved, a 0.1 mol/L to 0.5 mol/L (preferably 0.1 mol/L to 0.2 mol/L) sodium hydroxide solution is used to adjust the pH to 7.5 to 9.

In the above preparation process of the present invention, the NaOH solution may be added dropwise at room temperature or under heated conditions; those skilled in the art are able to select proper dripping conditions according to the actual needs.

Further, the preferred range of concentration of the resulting arsenic compound solution is 6 mg/mL to 10 mg/mL, and the most preferable is 8 mg/mL.

The arsenic compound solution prepared in the present invention, in which the solute mainly comprises sodium metaarsenite ($NaAsO_2$) and $As_2O_3$, can be used to prepare arsenic compound-loaded albumin nanoparticles with small particle sizes, good dispersion, and good stability.

The second objective of the invention is to provide arsenic compound-loaded albumin nanoparticles prepared with the arsenic compound solution, the arsenic compound-loaded albumin nanoparticles use HSA or BSA as skeleton material, which has good slow-releasing potential, to load the arsenic compound which has well-defined structure and good drug effects, therefore the arsenic compound-loaded albumin nanoparticles form a controlled release preparation that can improve drug effects and biocompatibility, and reduce toxicity and side effects.

In the present invention, the arsenic compound-loaded albumin nanoparticles are prepared by a method of solvent removing and physical curing, which is fast and simple and provides for high operability, uniform particle-size and a narrow particle-size distribution, etc.

The preparation method of the arsenic compound-loaded albumin nanoparticles comprises the following steps:

(1) preparing an albumin solution with deionized water and albumin which is human albumin or bovine albumin, and making the concentration of the albumin solution be from 0.01 g/mL to 0.02 g/mL;

(2) mixing the arsenic compound solution and the albumin solution with a mass ratio of $As_2O_3$ added to prepare the arsenic compound solution to the albumin ranging from 1:5 to 1:20, adjusting the pH value of the mixture to from 7.5 to 9 with a NaOH solution; and adding a dehydration agent, which is selected from the group consisting of ethanol, acetone, and any combination thereof, to the mixture with a volume ratio of the dehydrating agent to the albumin solution ranging from 2.0:1 to 3.5:1 while stirring, to obtain an emulsion;

(3) placing the emulsion in a water bath, and subjecting the emulsion to physical curing at a curing temperature between 40° C. and 90° C. for 10 min to 240 min, in order to obtain an emulsion of nanoparticles;

(4) subjecting the emulsion of nanoparticles to evaporation to remove the dehydrating agent, and then subjecting the resulting emulsion to centrifugal separation to obtain arsenic compound-loaded albumin nanoparticles.

In step (2), after the pH value has been adjusted to 7.5 to 9 with the NaOH solution, a NaCl solution is added until the final NaCl concentration is 5 mM to 10 mM, and then the dehydrating agent is added.

In step (2), it is preferable that the arsenic compound solution and the albumin solution are mixed with a mass ratio of $As_2O_3$ added to prepare the arsenic compound solution to the albumin ranging from 1:10 to 1:20; and the dehydrating agent is a mixture of ethanol and acetone with a volume ratio ranging from 1:0.05 to 1:20.

In step (3), the curing temperature is preferably between 40° C. and 80° C.; and the curing time is preferably between 10 min and 120 min.

In step (4), the dehydrating agent is preferably removed from the emulsion of nanoparticles with a method as follows: the emulsion of nanoparticles is placed in the environment of 30° C. to 50° C. water bath to be subjected to rotary evaporation to remove the dehydrating agent; the centrifugal separation specifically adopts the following steps: after removing the dehydrating agent, a equal volume of sterile deionized water is added to the emulsion of nanoparticles to obtain a mixture, the mixture is placed in a high-speed centrifuge, the centrifugation is carried out at 5° C., 14000~17000 rpm/min for 25 min to give solid precipitates, and the solid precipitates is washed 2~3 times to obtain arsenic compound-loaded albumin nanoparticles.

The third objective of the invention is to provide a freeze-dried preparation of arsenic compound-loaded albumin nanoparticles prepared with the arsenic compound solution; the arsenic compound-loaded albumin nanoparticles use HSA or BSA as skeleton material, which has good slow-releasing potential, to load the arsenic compound which has well-defined structure and good drug effects, therefore the freeze-dried preparation of arsenic compound-loaded albumin nanoparticles forms a controlled-release preparation that can improve drug effects and biocompatibility, and reduce toxicity and side effects.

The preparation process of the freeze-dried preparation of arsenic compound-loaded albumin nanoparticles comprises the following steps:

(a) preparing an albumin solution with deionized water and albumin which is human albumin or bovine albumin, and making the concentration of the albumin solution be from 0.01 g/mL to 0.02 g/mL;

(b) mixing the arsenic compound solution and the albumin solution with a mass ratio of $As_2O_3$ added to prepare the arsenic compound solution to the albumin ranging from 1:5 to 1:20, adjusting the pH value of the mixture to from 7.5 to 9 with a NaOH solution; and adding a dehydration agent, which is selected from the group consisting of ethanol, acetone, and any combination thereof, to the mixture with a volume ratio of the dehydrating agent to the albumin solution ranging from 2.0:1 to 3.5:1 while stirring, to obtain an emulsion;

(c) placing the emulsion in a water bath, and subjecting the emulsion to physical curing at a curing temperature between 40° C. and 90° C. for 10 min to 240 min, in order to obtain an emulsion of nanoparticles;

(d) subjecting the emulsion of nanoparticles to evaporation to remove the dehydrating agent, and then subjecting the resulting emulsion to centrifugal separation to obtain arsenic compound-loaded albumin nanoparticles;

(e) adding a cryoprotectant to the arsenic compound-loaded albumin nanoparticles with a mass ratio of the arsenic compound-loaded albumin nanoparticles to the cryoprotectant ranging from 1:3 to 1:5; and subjecting the mixture to freeze-drying to attain a freeze-dried preparation of arsenic compound-loaded albumin nanoparticles.

The steps (a)~(d) listed above, as they are identical to steps (1)-(4) of preparing the arsenic compound-loaded albumin nanoparticles, are not discussed here again.

In addition, in step (e), the cryoprotectant is selected from one or a combination of two of the following: mannitol, glucose, sucrose, glycine, trehalose, maltose, lactose; and the freeze-drying is conducted at a temperature between −80 and −40° C.

The freeze-dried preparation of arsenic compound-loaded albumin nanoparticles according to the invention, can be made to allow administration through injection by conventional pharmaceutical production processes. Because the carrier materials are easily attainable and affordable, it is suitable for preparing oral dosage forms, such as capsules, tablets, suspensions, etc.

Because the arsenic compound-loaded albumin nanoparticles and the freeze-dried preparation according to the invention load sodium metaarsenite ($NaAsO_2$) and $As_2O_3$, they can be widely used for the treatment of systemic lupus erythematosus (SLE); autoimmune category rheumatoid arthritis (RA); Sjogren's Syndrome, myasthenia gravis (MG); autoimmune thyroid diseases, autoimmune lung diseases (such as asthma) and other autoimmune diseases; insulin-dependent diabetes mellitus (IDDM; I diabetes); and be used in cancer chemotherapy.

Compared with the prior art, the present invention has the following advantages:

1) In the present invention, hydrochloric acid is not added during the preparation of the arsenic compound solution; as a result, the prepared arsenic compound has well-defined molecular structure and significant therapeutic effects, which not only can inhibit human B lymphoma cells, but also significantly inhibit human T lymphoma cells.

2) In the present invention, the arsenic compound-loaded HSA or BHA nanoparticles are prepared by a method of solvent removing and physical curing, without using surfactants and chemical cross-linking agents; compared with emulsification-heat curing method and solvent removing-chemical cross-linking curing method which are also used for preparing nanoparticles, the solvent removing and physical curing method is simple, rapid, and allows for easy expansion of operations, not to mention that the resulting nanoparticles are less than 200 nm in size, smooth and have a round shape, good dispersion, flexibility, and are easy to store steadily.

3) The arsenic compound-loaded nanoparticles and freeze-dried powder can release drug dosage at a constant rate, and make plasma drug concentration more stable than other sustained-release preparations, and can significantly increase patient compliance, thereby improving drug effects, biocompatibility and reducing toxicity and side-effects; compared with the sustained-release preparations prepared by a emulsification-chemical cross-linking method or a solvent removing-chemical cross-linking method, the arsenic compound-loaded HSA or BHA nanoparticles prepared in the present invention can be released over a longer period of time and form potential controlled-release nanoparticles preparations.

4) The nanoparticles prepared by the invention have a narrow size distribution, which is able to meet the demand for the size range of the drug as targeted drug delivery systems. And because the nanoparticles are prepared by a method of solvent removing and physical curing, the thermal denaturation temperature and time may only affect the stability, but will not affect the particle size and the number of surface amino groups [Weber C, Coester C, Kreuter J, et al. Desolvation process and surface characteristics of protein nanoparticles [J]. Int J Pharm. 2000.194 (a): 91.], so the resulting nanoparticles have more surface amino groups. Therefore, the nanoparticles of the present invention are good carriers for preparing active targeting drug delivery systems by coupling antibodies corresponding to various diseases, specifically, a monoclonal antibody having positive targeting ability is combined with surface amino groups of the nanoparticles by coupling, to obtain an active targeting preparation with positioning and transferring functions.

DESCRIPTIONS OF THE DRAWINGS

FIG. 1 is a TEM image of the arsenic compound-loaded HSA nanoparticles prepared in Example 3 (4×10000 times).

FIGS. 2A1, 2A2 and 2A3 are atomic force microscopy images (scanning probe electron microscope) of the emulsion of arsenic compound-loaded HSA nanoparticles prepared in Example 3, as can be seen from the images, the nanoparticles have spherical morphology, circular dispersion, smooth surface, and uniform particle size distribution.

FIG. 3 is an atomic force microscopy image of the emulsion of arsenic compound-loaded HSA nanoparticles prepared in Example 5.

FIG. 4A1 is an atomic force microscopy image of the emulsion of arsenic compound-loaded HSA nanoparticles prepared in Example 4; FIG. 4A2 is an atomic force microscopy image in the same location as FIG. 4A1; FIG. 4A3 is an atomic force microscopy image of the sample restored from the same sample of FIG. 4A1.

FIG. 5A is an atomic force microscopy image of the emulsion of arsenic compound-loaded HSA nanoparticles without the dehydrating agent prepared in Example 3 which has been placed at room temperature for 6 months, FIG. 5B is an atomic force microscopy image of the freeze-dried powder prepared in Example 3 which has been stored in a 4° C. refrigerator for 6 months.

FIG. 6 is a particle diameter distribution map of the arsenic compound-loaded HSA nanoparticles prepared in Example 3.

FIG. 7 is a in vitro drug release curve of the arsenic compound-loaded HSA nanoparticles prepared in Example 4.

FIG. 8 is an atomic force microscopy image of the emulsion of arsenic compound-loaded BSA nanoparticles prepared in Example 2.

FIG. 9 is an atomic force microscopy image of the freeze-dried powder sample of arsenic compound-loaded BSA nanoparticles prepared in Example 3 which has been stored in 4° C. refrigerator for 6 months.

FIG. 10 is a cell count graph of apoptosis detected by flow cytometry, A is the control group, FIG. 10B1-FIG. 10B4 respectively correspond to the arsenic compound-treated groups with $As_2O_3$ concentration of 0.2. μg/ml, 0.4 μg/ml, 0.8 μg/ml, and 1.6 μg/ml.

FIG. 11 is a histogram of apoptosis detected by flow cytometry.

FIG. 12A is an apoptotic body picture of human T cell lymphoma cell lines jurkat cells of the control group, and FIG. 12B is an apoptotic body picture of human T cell lymphoma cell lines jurkat cells treated with arsenic compound ($As_2O_3$ 0.8 μg/mg).

FIG. 13A, B, C are cellular mitochondria pictures of the cells in control group; and A, B, C respectively correspond to a conventional filter, a red fluorescence, a green fluorescence picture taken in the same field of view.

FIG. 14 A, B, C are cellular mitochondria pictures of the cells in the arsenic compound treated group ($As_2O_3$ 0.4 μg/mg); and A, B, C respectively correspond to a conventional filter, a red fluorescence, a green fluorescence picture taken in the same field of view.

Figure 15A:
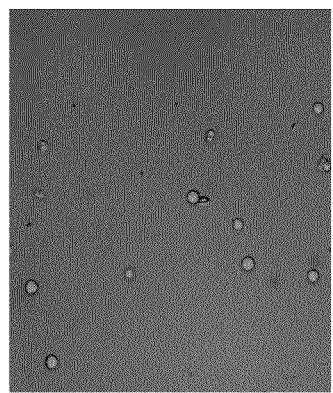

FIG. 15 A, B, C are cellular mitochondria pictures of the cells of the arsenic compound treated group ($As_2O_3$ 0.8 μg/mg), and A, B, C respectively correspond to a conventional filter, a red fluorescence, a green fluorescence picture taken in the same field of view.

MODE OF CARRYING OUT THE INVENTION

The present invention will be illustrated by reference to the following examples. However, the examples are only for illustration without limiting the scope of the present invention.

Example 1

Preparation of the Arsenic Compound Solution 120 mg of $As_2O_3$ powder (99.9% of purity) is accurately weighed and added into a flask with 8 ml of sterile deionized water, to create a suspension. The suspension is heated, a 1 mol/L NaOH solution is added dropwise until the powder has completely dissolved; subsequently a 0.1 mol/L NaOH solution is added to adjust the pH level to 8.4, and sterile deionized water is added to obtain a final volume of 15 ml of arsenic compound solution, with a concentration of 8 mg/ml in terms of the $As_2O_3$ powder added.

Example 2

Preparation of Arsenic Compound-Loaded HSA or BSA Nanoparticles

① 0.45 ml of arsenic compound solution prepared in Example 1 is absorbed;
② 60 mg of HSA or BSA and sterile deionized water are mixed to create an albumin solution with concentration of 1.2% (g/ml). The albumin solution is then filtered through a 0.22μ membrane and into a sterile container;
③ the arsenic compound solution and the albumin solution are mixed, then a 0.1 mol/L NaOH solution is added again to adjust the pH to 7.6; then a 50 mmol/L NaCl solution is added until the final NaCl concentration is 10 mmol/L. A dehydrating agent is added at a rate of 1 mL/min at room temperature (anywhere from 25-30° C.) with stirring at a rate of 1000 rpm. The dehydrating agent is a mixture of ethanol and acetone with a volume ratio of 3:1, has a volume of about 12 ml and is added until the emulsion appears. After that, stirring continues for 30 min, resulting in an opalescent emulsion;
④ the opalescent emulsion is placed in a water bath and subjected to physical curing. The physical curing is carried out at the stirring rate of 1000 rpm, 65° C. for 60 min, to obtain an emulsion of nanoparticles;
⑤ The emulsion of nanoparticles is placed in a 40° C. water bath, and the dehydrating agent is removed by evaporation under reduced pressure to obtain a emulsion of nanoparticles without the dehydrating agent;
⑥ After removal of the dehydrating agent, an equal volume of sterile deionized water is added to the emulsion of nanoparticles without dehydrating agent. The emulsion is then placed in a high-speed centrifuge, subjected to centrifugation at 5° C., 14000 rpm/min for 25 min and washed with sterile deionized water 2~3 times to obtain arsenic compound-loaded HSA or BSA nanoparticles;
⑦ The nanoparticles are suspended with sterile deionized water, then a lactose solution is added until the final lactose concentration is 4% and the mass ratio of the albumin nanoparticles to the lactose is 1:3 to 1:5, and the obtained mixture is freeze-dried at −51° C., whereby a freeze-dried powder preparation of arsenic compound-loaded HSA, BSA nanoparticles is obtained.

Example 3

The differences between this example and Example 2 are as follows, a 0.1 mol/L NaOH solution is used to adjust pH to 8.0; the volume of the dehydrating agent is about 14 ml; physical curing temperature is 70° C.; and the time required for curing is 60 min. The other steps are the same as Example 2.

Example 4

The differences between this example and Example 2 are as follows, a 0.1 mol/L NaOH solution is used to adjust the pH to 8.4; the dehydrating agent has a volume of about 16 ml; physical curing temperature is 70° C., and the time required for solidification is 40 min. The other steps are the same as the aforementioned Example 2.

Example 5

The differences between this example and Example 2 are as follows, 50 mg of HSA or BSA and sterile deionized water are mixed to prepare an albumin solution with a concentration of 1.0% (g/ml), and the albumin solution is filtered through a 0.22μ membrane and into a sterile container; the arsenic compound solution and the albumin solution are mixed, then a 0.1 mol/L NaOH solution is used to adjust the pH to 8.8. The dehydrating agent has a volume of about 17.5 ml; physical curing temperature is at 75° C., and the time required for curing is 25 min. Others are the same as Example 2.

The test items of the arsenic compound-loaded HSA, BSA nanoparticles are as follows:
1. the morphology of the nanoparticles observed by transmission electron microscopy The Morphology of the nanoparticles is observed by Transmission Electron Microscopy: the dispersion of the sample is dripped on the copper mesh, stained with a 2% phosphotungstic acid, naturally dried at room temperature, and the morphology of the nanoparticles are observed and photographed.

FIG. 1 is a transmission electron microscope image of the arsenic compound-loaded HSA nanoparticles prepared in Example 3 (4×10000 times). As seen in FIG. 1, the nanoparticles have a spherical shape, smooth edges, are finely-dispersed, and have relatively uniform particle size distribution.

2. The morphology of the nanoparticles observed by atomic force (scanning probe microscope)

An appropriately diluted emulsion of nanoparticles is dripped onto a test platform of a newly stripped mica sheet, naturally dried at room temperature, and tested by a Shimadzu scanning probe microscope SPM-9600.

FIGS. 2A1, 2A2 and 2A3 are atomic force microscopy images of the emulsion of arsenic compound-loaded HSA nanoparticles prepared in Example 3; as can be seen, the nanoparticles have spherical morphology, circular dispersion, smooth surface, and relatively uniform particle size distribution.

FIG. 3 is an atomic force microscopy image of the emulsion of arsenic compound-loaded HSA nanoparticles prepared in Example 5; as shown, the nanoparticles prepared in Example 5 have spherical morphology, uniform distribution, and a particle diameter of less than 90 nm.

FIG. 4A1 is an atomic force microscopy image of the emulsion of arsenic compound-loaded HSA nanoparticles prepared in Example 4. Four samples of the arsenic compound-loaded HSA nanoparticles are treated simultaneously, washed, centrifuged under the same condition, and diluted to prepare atomic force samples for measuring. As shown in FIG. 4A1, three particles regularly overlaps to form a big particle. In order to observe the figure more clearly, a special mode is set to observe the same position of the atomic force microscopy image as FIG. 4A1. As clearly shown in FIG. 4A2, three particles regularly overlaps to form a big particle. FIG. 4A3 is an atomic force microscopy image of the sample restored from the same sample of FIG. 4A1. FIG. 4A1-4A2 show the morphological changes: 1) since the particle size of nanoparticles according to the present invention is 200 nm or less, high-speed centrifugation is required for washing and separation, which may cause compressive deformation of the morphology of nanoparticles and make the protein mesh larger resulting in drugs easier to seep out from the protein mesh, so it is presumed that high-speed centrifugation may lead to an increase in the concentration of free arsenic compound and a reduction in drug loading and encapsulation efficiency. 2) However, FIG. 4A3 shows after being diluted with water and in the water-diluted sample for a period, the compressive deformed nanoparticles has been restored to their original spherical shape, which means the arsenic compound-loaded albumin nanoparticles prepared in the present invention have flexibility and strong plasticity. As we know, the nanospheres and microparticles prepared by chemical crosslinking with glutaraldehyde can easily be squeezed and ruptured by high-speed centrifugation, which results in drugs seeping out and a reduction in drug loading and encapsulation efficiency, so there are essential distinctions between the nanoparticles prepared in the present invention and the nanospheres and microparticles prepared by chemical crosslinking with glutaraldehyde.

Figure 8:
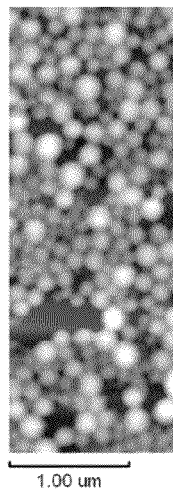

FIG. 8 is an atomic force microscopy image of the emulsion of arsenic compound-loaded BSA nanoparticles prepared in Example 2.

3. Determination of Particle Size

Particle Size is Measured by Atomic Force Measurement Software.

Figure 6:
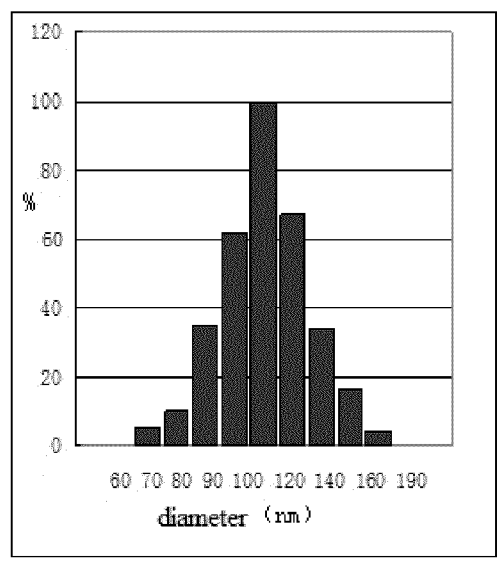

FIG. 6 is a particle diameter distribution map of the arsenic compound-loaded HSA nanoparticles prepared in Example 3. The particle size is measured with atomic force measurement software; the results of 824 nanoparticles are analyzed and a size distribution map is drawn; the results show that the average particle diameter of nanoparticles is 117 nm; a span is calculated: (Span)=(D90−D10)/D50=0.596, showing that the nanoparticles prepared by the present invention have a narrow particle size distribution. Nanoparticles with average particle diameter of below 200 nm can pass through capillaries and meet the demand for the size of drug of targeted drug delivery systems.

4. Drawing of a Standard Curve and Measurement of Drug Loading and Encapsulation Efficiency 4-1. Drawing of a Standard Curve The arsenic compound solution is precisely diluted to give solutions with different concentrations in terms of $As_2O_3$ added: 0, 0.05, 0.2, 1.0, 2.0, 4.0, 6.0, 8.0, 10 mg/L. The data of the solutions with different concentrations are determined by Thermo Scientific inductively coupled plasma emission spectrometry ICP-OES icap-6000 to obtain a standard curve; and the correlation coefficient is 0.999937. the concentration in terms of $As_2O_3$ added in each sample can be obtained with the $As_2O_3$ standard curve.

4-2. The Measurement of Drug Loading and Encapsulation Efficiency

An appropriate amount of the emulsion of nanoparticles is mixed with an equal volume of deionized water, then the mixture is placed in high-speed centrifuge and centrifuged at 5° C., 14 000 rpm/min for 25 min to give precipitate and supernatant; the precipitate is washed twice with deionized water, and the supernatant is combined and mixed. A same amount of the emulsion of nanoparticles and the combined supernatant are respectively quantitatively absorbed and placed into a tetrafluoroethylene tube, added with concentrated nitric acid for thermophilic digestion; the thermophilic digested sample is transferred to a volumetric flask and diluted to 50 ml with deionized water. The data of the emulsion and the supernatant are measured respectively by using Thermo Scientific inductively coupled plasma emission spectrometry ICP-OES icap-6000; then the amounts of $As_2O_3$ in the emulsion and free $As_2O_3$ in the combined supernatant are obtained according to the standard curve, and finally the drug loading and encapsulation rate are calculated. The drug loading, encapsulation efficiency of HSA nanoparticles prepared in Example 3 and the drug loading, encapsulation efficiency, and Zeta potential (my) of BSA nanoparticles obtained in Example 2 are shown in Table 1 below.

TABLE 1

| | partial characterization parameters of the arsenic compound-loaded albumin nanoparticles | | | | |
|---|---|---|---|---|---|
| albumin | Average particle size | Particle size range | Encapsulation efficiency (%) | Drug loading (%) | Zeta potential (mv) |
| HSA | 117 nm | 58-202 nm | 56.87 | 3.75 | |
| BSA | 144 nm | 92-205 nm | 48.7 | 3.3 | −38 ± 0.3 |

5. Drug Release Behavior In Vitro of the Nanoparticles

The drug release behavior in vitro of the albumin nanoparticles is investigated by dynamic dialysis. 1 ml of the emulsion of nanoparticles is precisely absorbed, subjected to high speed centrifugation (at 5° C., 14 000 rpm/min for 25 min) and washed (twice, with deionized water) to give nanoparticles. The nanoparticles are successively suspended and washed with 3 ml of sterile deionized water, and then placed into a dialysis bag. The ends of the bag are tightened. The dialysis bag is placed into a bottle with 27 ml sterile deionized water, which is then placed in a shaker at 37° C. with an oscillation frequency of 60 r/min for drug dissolution. 2 ml of the sustained-release fluid is sampled in 2 h, 4.5 h, 1 d, 2 d, 3 d, 4 d, 5 d, 6 d, 7 d, 8 d, 9 d, and 10 d respectively, meanwhile a corresponding volume of sterile deionized water is supplemented. The sustained-release fluid is diluted, and placed in the inductively coupled plasma emission spectrometry ICP-OES icap-6000 instrument for measuring the release amount of $As_2O_3$. Then calculate the cumulative release percentage and draw a in vitro release chart with time as the abscissa and $As_2O_3$ cumulative release rate as the ordinate.

Figure 7:
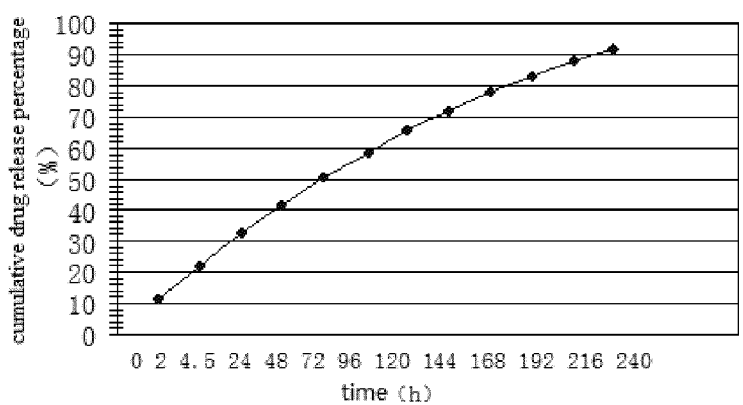

FIG. 7 is a curve chart showing in vitro drug release behavior of the arsenic compound-loaded HSA nanoparticles prepared in Example 4. The result of FIG. 7 shows as follows: the drug release rate is 11.58% within the first 2 hours and there is no burst effect; the release is slow and sustained; the cumulative release rate reaches 91.7% in 10 days, therefore the drug release time is considered to be about 10 days. The result of FIG. 7 is calculated by Mt/M∞=Rt (zero-order equations) [Chinese Pharmacopoeia 2005, Volume II, appendix, p180, <<released drug data available zero-order equations fitting of controlled release formulations>>], and mathematical equations for cumulative release at different molecular weights and different time described in [Xie Xiuqiong, the development and application of new preparation of traditional Chinese Medicine, 3rd edition, p488-499, table 6-161], and the calculating result is: $R2=0.9802$, $R=0.990$ ($Y=7.2454x+10.721$). The result shows that the release behavior in vitro of the arsenic compound-loaded albumin nanoparticles of the present invention is according with zero-order release and thus the arsenic compound-loaded albumin nanoparticles form controlled-release preparations.

6. Investigation of Stability In Vitro of the Arsenic Compound-Loaded HSA Nanoparticles The emulsion of arsenic compound-loaded HSA nanoparticles prepared in Example 3 is placed at room temperature for 6 months and then washed with deionized water to prepare testing samples of the emulsion of nanoparticles; the freeze-dried powder of arsenic compound-loaded BSA nanoparticles prepared in Example 2 and the freeze-dried powder of arsenic compound-loaded HSA nanoparticles prepared in Example 3 are stored in a refrigerator at 4° C. for 6 months, then washed with deionized water to prepare testing samples of the freeze-dried powder of nanoparticles. The stability of the emulsion of nanoparticles and the freeze-dried powder of nanoparticles are respectively investigated:

6-1. Observation of the Appearance

The emulsion of nanoparticles appears as an opalescent colloidal suspension.

The appearance of freeze-dried powder of nanoparticles maintains the original volume, with no collapse, no shrink, smooth surface, uniform color, and fine texture.

6-2. Evaluation for Redispersibility of the Freeze-Dried Powder of Nanoparticles After the freeze-dried powder of arsenic compound-loaded albumin nanoparticles has been stored at 4° C. for 6 months, it remains white and fluffy. The freeze-dried powder of nanoparticles is added with deionized water or saline and shaken for 20 seconds to obtain a homogeneously dispersed and suspended emulsion.

6-3. Morphology by Atomic Force Microscope

After the emulsion of arsenic compound-loaded HSA nanoparticles has been stored at room temperature for 6 months, the results of atomic force detection show that there is no aggregation or adhesion phenomenon between nanoparticles, and the average particle diameter has not increased, as shown in FIG. 5A.

FIG. 5B is a atomic force microscopy image of the freeze-dried powder in Example 3 which has been stored in 4° C. refrigerator for 6 months. As can be shown, the nanoparticles have round shape, uniform size, without aggregation and adhesion phenomena, and almost unchanged particle size. Compared FIG. 5A with 5B, FIG. 5B shows that the morphology of emulsion of nanoparticles remains consistent with FIG. 5A, indicating that the freeze-dried powder of arsenic compound-loaded HSA nanoparticles prepared in the present invention has good stability.

Figure 9:
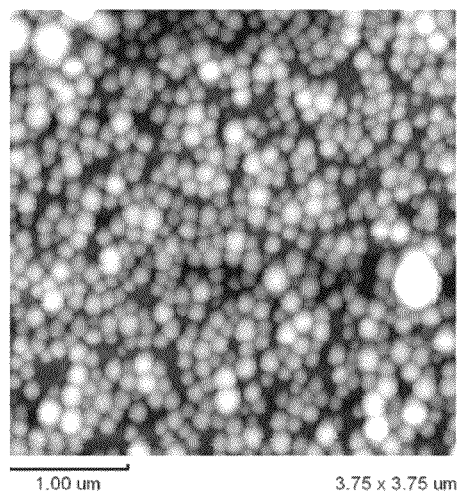

FIG. 9 is a atomic force microscopic image of the freeze-dried powder sample prepared in Example 2 which has been stored in 4° C. refrigerator for 6 months. As can be shown, FIG. 9 shows the nanoparticles have a spherical shape, smooth edges, and fine-dispersion between particles, indicating that the freeze-dried powder of arsenic compound-loaded BSA nanoparticles prepared in the present invention has good stability.

Pharmacodynamic Experiments:

Drug effects of the arsenic compound-loaded HSA, BSA nanoparticles prepared in the present invention are described further below. The arsenic compound-loaded HSA, BSA nanoparticles prepared by the present invention release over a long time, and are unsuitable for short-term pharmacodynamic test in vitro; therefore, the same arsenic compound solution used for preparing the arsenic compound-loaded HSA, BSA nanoparticles is selected to be used in the in vitro experiments to study the effects of the arsenic compound on T lymphocytes, B lymphocytes:

1. Cell Culture

Human lymphoma cell line cells are cultured in RPMI 1640 culture medium containing 10% new-born calf serum, placed in a 5% $CO_2$ incubator, and cultured at 37° C. with saturated humidity. The medium is changed every 1-2 days. When the cells grow well, the drug is applied to the cells.

2. The Experiment Grouping 2.1

The growing well human B lymphoma cell line Daudi cells are cultured in a 24-well plate; each well is inoculated with 1 ml of the cell culture with a cell density of $1.5 \times 10^5$/ml, and they are divided into experimental and control groups. The experimental groups are divided into 0.1, 0.2, 0.8 μg/ml $As_2O_3$ groups, the cells in each group are treated with the arsenic compound solution with respective concentration in terms of $As_2O_3$ added, for example, the cells in 0.8 μg/ml $As_2O_3$ group are treated with 0.8 μg/ml arsenic compound solution, and the arsenic compound solutions with different concentration are prepared by the following method: the arsenic compound solution obtained in Example 1 is first diluted with deionized water to 80 μg/ml, and then diluted to the desired concentration with 1640 culture fluid to obtain arsenic compound solutions with different concentration. The control group is added with a equal volume of culture fluid. The 24-well plate is placed in a 5% $CO_2$ incubator, the cells are cultured at 37° C. and saturated humidity for a predetermined time, and then detected correspondingly. The cell suspensions are stained by physiological saline solution of 0.3% trypan blue for counting survival, dead cells; and the results are shown in Table 2:

TABLE 2

Inhibitory effect of arsenic trioxide with different concentrations on the proliferation of Daudi cells

| $As_2O_3$ μg/ml | 20 h ($10^5$/ml) the number of survival cells | Death rate (%) | 68 h ($10^5$/ml) the number of survival cells | Death rate (%) |
|---|---|---|---|---|
| 0 μg/ml | 1.31 | 21 | 4.10 | 17 |
| 0.1 μg/ml | 1.40 | 33 | 1.24 | 66 |
| 0.2 μg/ml | 1.27 | 44 | 0.77 | 75 |
| 0.4 μg/ml | 0.99 | 56 | 0.30 | 88 |
| 0.8 μg/ml | 0.58 | 68 | 0.06 | 98 |

The results in Table 2 show that $As_2O_3$ can significantly reduce the cell viability of malignant B lymphoma cell line Daudi cells, inhibit the cell growth of B lymphoma cell line Daudi cells, and cause morphological changes such as cell apoptosis, presenting dose dependence.

2.2

The human T-cell lymphoma cell line jurkat cells in exponential growth phase are inoculated into a 24-well plate and cultured; 1 ml of jurkat cells with a cell density of $2\chi10^5$/ml are inoculated into each well, and the 24-well plate is placed in a 37° C., 5% $CO_2$ incubator. Jurkat cells are treated with the arsenic compound solutions with different final $As_2O_3$ concentrations of 0, 0.2, 0.4, 0.8 μg/ml for 24, 48, 72 hours, and the arsenic compound solutions with different final $As_2O_3$ concentrations are prepared as follows: the arsenic compound solution obtained in Example 1 is first diluted with deionized water to 80 μg/ml, and then diluted to the desired concentration with 1640 culture fluid. The treated cell suspensions are stained with physiological saline solution of 0.3% trypan blue for determining survival, dead cell count, and the results shown in Table 3:

TABLE 3 inhibitory effect of arsenic trioxide with different concentrations on the proliferation of jurkat cells

| $As_2O_3$ μg/ml | 24 h/ml total number of the cells | cells $10^5$ the number of survival cells | Death rate (%) | 48 h/ml total number of the cells | cells $10^5$ the number of survival cells | Death rate (%) | 72 h/ml total number of the cells | cells $10^5$ the number of survival cells | Death rate (%) |
|---|---|---|---|---|---|---|---|---|---|
| 0 | 9.32 | 9.16 | 1.8 | 13.70 | 13.31 | 2.8 | 16.39 | 15.51 | 5.4 |
| 0.2 | 7.98 | 7.56 | 5.2 | 12.18 | 10.29 | 16 | 9.19 | 4.95 | 46.1 |
| 0.4 | 6.57 | 4.87 | 25.9 | 7.73 | 5.12 | 34 | 7.45 | 3.66 | 50.9 |
| 0.8 | 5.53 | 2.92 | 47.3 | 5.61 | 2.5 | 55 | 6.08 | 1.84 | 69.7 |

The results in Table 3 show that, the arsenic compound has a significant inhibitory effect on the proliferation of human T lymphoma cell line jurkat cells. After 24 h of treatment, correlation coefficients between the number of survival cells, the death rate and the concentration are respectively −0.978, 0.981; the number of survival cells and the concentration have a negative correlation (P<0.05), and the death rate and the concentration have a positive correlation (P<0.05). After 48 h of treatment, correlation coefficients between the number of survival cells, the death rate, and the concentration are respectively −0.961, 0.994, the number of survival cells and the concentration have a negative correlation (P<0.05), and the death rate and the concentration have a positive correlation (P<0.01). By 72 hours, the proliferation of the normal cells would be affected due to poor nutrition. Specifically, the cell proliferation after being treated for 48 h is 47% greater than that after being treated for 24 h, however, the cell proliferation after being treated for 72 hours is only 20% greater than that after being treated for 48 hours, making the correlations between the number of survival cells, the death rate and the concentration after being treated for 72 h decreased, which are respectively −0.819, 0.905. correlation coefficients between the death rate after treated with different concentrations of arsenic compound and the time 24, 48, 72 h are respectively 0.969, 0.965, 0.980, 0.984, the death rate and the time have a positive correlation (P<0.05), and the death rate is dependent on the time.

Meanwhile, by comparing the results in Table 2 with the results in Table 3, it has shown that the human B cell lymphoma cell line Daudi cells are more sensitive to $As_2O_3$-induced cell death than human T lymphoma cell lines jurkat cells.

2.3. Cell Apoptosis Detected by Flow Cytometry

The human T-cell lymphoma cell line jurkat cells in exponential growth phase are inoculated into a 6-well plate and cultured; 3 ml of jurkat cells with a cell density of $2\chi10^5$/ml are inoculated into each well, and the 6-well plate is placed in a 37° C., 5% $CO_2$ incubator. After being cultured for 4 hours, jurkat cells are treated with the arsenic compound solution with different final $As_2O_3$ concentrations of 0, 0.2, 0.4, 0.8 μg/ml, and the arsenic compound solutions with different final $As_2O_3$ concentrations are prepared as follows: the arsenic compound solution obtained in Example 1 is first diluted with deionized water to 80 μg/ml, and then diluted to the desired concentration with 1640 culture fluid. The control group is treated with an equivalent volume of 1640 culture fluid. After being treated for 44 hours, jurkat cells in the experimental and control groups with a cell density of $1\chi10^6$/ml are collected, and apoptosis is studied by AnnexinV/PI double staining flow cytometry.)

Cell apoptosis detected by AnnexinV/PI double staining flow cytometry:

The cells in the experimental and control groups with a density of $1\chi10^6$ jurkat cells/ml are respectively collected, washed twice with PBS, and subjected to centrifugation at 1000 r/min for 5 min, and the supernatant is discarded. Each 100 μl of the cell suspension is mixed with 5 μL Annexin-V, and then mixed with 2 μL of propidium iodide (PI). The mixtures are incubated at room temperature and dark conditions for 15 min, then mixed with 400 μl of 1χAnnexin-V binding buffer after incubation, and placed in an ice water bath. Meanwhile, the flow cytometry instrument is subjected to regular correct, besides, the normal cells in the control group are collected to prepare positive control and negative control for dead cells and survival apoptotic cells to correct the instrument, so that the instrument has more precise control threshold for different characteristic samples. Then, the stained cells were detected by flow cytometry; and similar results are obtained by experiment repeated:

TABLE 4 the effects of arsenic trioxide with different concentrations on apoptosis of jurkat cells

| $As_2O_3$ µg/ml | Survival rate (%) | Early apoptotic rate (%) | Apoptotic rate (%) | Early apoptotic rate + Apoptotic rate (%) |
|---|---|---|---|---|
| 0 µg/ml | 97.2 | 2.8 | | 2.8 |
| 0.2. µg/ml | 92.8 | 6.5 | 0.7 | 7.2 |
| 0.4. µg/ml | 84.5 | 14.1 | 1.4 | 15.5 |
| 0.8 µg/ml | 69.0 | 26.1 | 5.0 | 31.0 |
| 1.6 µg/ml | 33.4 | 50.8 | 15.8 | 66.6 |

The results in Table 4 show that, with regard to $As_2O_3$-induced human T lymphoma cell line jurkat cell apoptosis, jurkat cell apoptotoc rate is positively correlated with the concentration (R=0.997 (P<0.01)), demonstrating a dose-dependent manner.

2.4. Observation of Cell Morphology

Human B lymphoma cell line Daudi cells and human T lymphoma cell line jurkat cells in the control group and $As_2O_3$-treated group (0.8 µg/mg) which have been cultured for 24 h are collected to prepare smears, Wright-Giemsa stained, and observed under a light microscope to determine the morphological changes of cells.

Detection of Apoptotic Bodies, Mitochondria 1) apoptotic bodies: human B lymphoma cell line Daudi cells and human T-cell lymphoma cell line jurkat cells in the control group and in the $As_2O_3$-treated group which have been cultured or treated for 24 h are collected to prepare smears, subjected to the detection of apoptotic bodies and photographed. The results are shown in FIGS. 12A and 12B; FIG. 12A is a light microscopy image of apoptotic bodies of human T cell lymphoma cell line jurkat cells in the control group; and FIG. 12B is a light microscopy image of apoptotic bodies of human T cell lymphoma cell line jurkat cells treated with 0.8 µg/mg $As_2O_3$, and the 0.8 µg/mg $As_2O_3$ is prepared as follows: the arsenic compound solution obtained in Example 1 is first diluted with deionized water to 80 µg/ml, and then diluted to 0.8 µg/mg with 1640 culture fluid. As can be seen, after being treated with $As_2O_3$ for 24 h, early apoptotic changes such as shrinkage and nuclear condensation occur in some cells, and nuclear fragmentation, cellular debris and apoptotic bodies appear.

2) Mitochondrial Observation:

Beyotime mitochondrial membrane potential detection kit (JC-1) is used; after the cells have been labeled with the fluorescent probe, they can be observed with a fluorescence microscope using conventional settings for observing red and green fluorescence, and photographed.

Measurement principle: The JC-1 fluorescent probe is used to detect mitochondrial potential; when the mitochondrial membrane potential is high, JC-1 aggregates in the mitochondrial matrix to form a polymer, which can produce red fluorescence; when the mitochondrial membrane potential is low, JC-1 can not aggregate in the mitochondrial matrix or the aggregation decreases, in this case, JC-1 exists in monomeric form and generates green fluorescence.

100 µl of suspension cultured cell liquid is centrifugalized and washed to obtain a sample. The sample is made into smears and observed by fluorescence microscopy, and three pictures are taken respectively by using conventional filter, red fluorescence, and green fluorescence sets in the same field of view. FIGS. 13 A, B, and C are mitochondrial pictures of the normal control group; and FIG. 14 A, B, C are mitochondrial pictures of the 0.4 µg/mg $As_2O_3$-treated group, and the 0.4 m/mg $As_2O_3$ is prepared as follows: the arsenic compound solution obtained in Example 1 is first diluted with deionized water to 80 µg/ml, and then diluted to 0.4 µg/mg with 1640 culture fluid; FIG. 15 A, B, C are mitochondrial pictures of the 0.8 µg/mg $As_2O_3$-treated group, and the 0.8 µg/mg $As_2O_3$ is prepared as follows: the arsenic compound solution obtained in Example 1 is first diluted with deionized water to 80 µg/ml, and then diluted to 0.8 µg/mg with 1640 culture fluid.

Figure 15B:
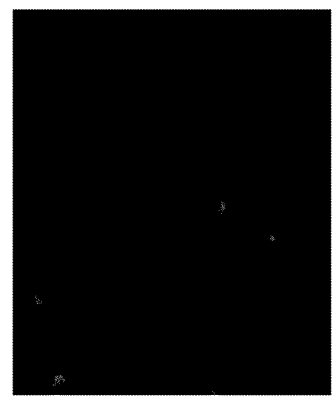
Figure 15C:
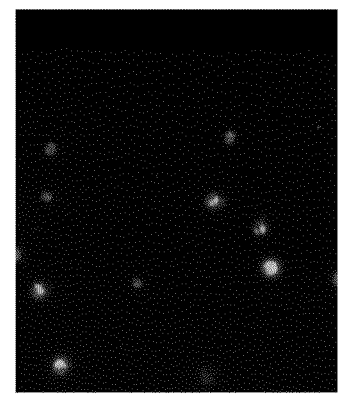

By comparing FIG. 13A with FIG. 14A, it is showed that the number of the cells in the 0.4 µg/m $As_2O_3$ treated group has decreased significantly; and changes such as significantly decreased cell volume, flattened cell morphology, and etc occur; the shape of the cells is not so full and stereoscopic as the shape of the cells in control group. FIG. 13B, FIG. 14B and FIG. 15B show that, compared with the cells in the control group, the number of the cells in the 0.4 µg/m $As_2O_3$ treated group and the red fluorescence intensity of JC-1 in the mitochondria of the cells have decreased significantly; and compared with the cells in the 0.4 µg/m $As_2O_3$ treated group, the number of the cells in the 0.8 µg/mg $As_2O_3$ treated group and red fluorescence intensity in the cells have also decreased significantly. FIG. 13C, FIG. 14C and FIG. 15C show that green fluorescence intensity increases relatively.

The results show that the normal control group has many cells per unit area (observed in the same field of view at the same magnification), and the red fluorescence intensity of JC-1 in many cells increases, while the green fluorescence intensity in the same cell relatively decreases, weakens. Compared with the cells in the control group, the number of the cells in the 0.4 µg/m $As_2O_3$ treated group and the red fluorescence intensity of JC-1 in the mitochondria of the cells decrease significantly; and compared with the cells in the 0.4 µg/m $As_2O_3$ treated group, the number of the cells in the 0.8 µg/mg $As_2O_3$ treated group and red fluorescence intensity in the cells also decrease significantly; and green fluorescence intensity increases relatively.

The results of mitochondrial observation demonstrate that the number of the cells in the $As_2O_3$ treated group and the red fluorescence intensity of JC-1 in the mitochondria of the cells decrease significantly, presenting dose dependence.

Arsenic is a cell protoplasmic poison; trivalent arsenic is a complexing agent of thiol (—SH), and can inhibit the activity of enzymes by reacting with the thiol in the enzyme molecules. Mitochondrion is the most sensitive organelle for arsenic, after trivalent arsenic consumes hydrophilic thiol within the mitochondrion, the ion balance and generation of oxidization products in mitochondria are inhibited, resulting in interference with mitochondrial energy metabolism and cellular dysfunction.

Mitochondria is the powerhouse necessary for cell survival; the analysis on the above experimental results further illustrates that, $As_2O_3$ inhibits human T lymphoma cell lines jurkat cell growth and induces cell apoptosis, possibly by making mitochondrial membrane potential collapsed and inducing apoptosis.

COMPARATIVE EXAMPLE

According to Chinese patent CN1370540A, human malignant B cell lymphoma cell line Raji cells with a cell density of $2.0 \times 10^5$/ml, were treated with $As_2O_3$ at a concentration of 0.5, 1.0, 2.0 µmol/L for 24, 48, 72 hours and the number of active cells was measured. The results showed that 0.5~2.0 µmol/L $As_2O_3$ inhibited cell growth in a dose dependent manner; but for human T-cell lymphoma cell line jurkat cells, with a cell density of $2.0\times10^5$/ml, $As_2O_3$ at the concentration of 0.5, 1.0, 2.0, 4.0 µmol/L did not inhibit cell growth.

Compared with Chinese patent CN1370540A: the arsenic compound solution prepared by the present invention has an inhibiting effect not only on the cell growth of human B cell lymphoma cell line Daudi cells, but also on the cell growth of human T cell lymphoma cell line jurkat cells. The human T-cell lymphoma cell line jurkat cells with the same cell density of $2.0\times10^5$/ml are also used in the experiments of the present invention, and treated with the same concentration (final concentration of 0.2, 0.4, 0.8 µg/ml) of $As_2O_3$ for 24, 48, 72 h, then the number of active cells is measured, and the results show that, 0.2-0.8 µg/ml $As_2O_3$ can inhibit cell growth, death rate and time have a positive correlation (P<0.05), presenting death rate is time-dependent. The results are shown in Table 2, Table 3, Table 4, FIG. 12A, FIG. 12B, FIG. 13, FIG. 14 and FIG. 15, which show that the arsenic compound solution prepared by the present invention has advantages over the prior art.

The invention claimed is:

1. An arsenic compound solution, which is prepared by a process consisting of: adding $As_2O_3$ powder in sterile deionized water to obtain a suspension, in which 6 to 25 mg of $As_2O_3$ powder are added in every mL of sterile deionized water; dripping an NaOH solution into the obtained suspension until the powder is fully dissolved and adding additional NaOH until the pH of the solution is 7.5 to 9, and making the concentration of the obtained arsenic compound solution be 5 to 20 mg/mL in terms of the added $As_2O_3$.

2. The arsenic compound solution according to claim 1, wherein a 1 to 6 mol/L sodium hydroxide solution is dripped to the obtained suspension until the powder is fully dissolved, and wherein the pH of the solution is 7.5 to 9 with a 0.1 to 0.5 mol/L sodium hydroxide solution.

3. The arsenic compound solution according to claim 1, wherein a 1 to 2 mol/L sodium hydroxide solution is dripped to the obtained suspension until the powder is fully dissolved, and wherein the pH of the solution is 7.5 to 9 with a 0.1 to 0.2 mol/L sodium hydroxide solution, and the concentration of the obtained arsenic compound solution is made to be 6 to 10 mg/mL in terms of the added $As_2O_3$.

\* \* \* \* \*